United States Patent
Ohinata et al.

(10) Patent No.: US 12,297,240 B2
(45) Date of Patent: *May 13, 2025

(54) PEPTIDE

(71) Applicants: Kyoto University, Kyoto (JP); Kazusa DNA Research Institute, Kisarazu (JP)

(72) Inventors: Kousaku Ohinata, Kyoto (JP); Yukiha Mori, Kyoto (JP); Hideyuki Suzuki, Kisarazu (JP)

(73) Assignees: Kyoto University, Kyoto (JP); Kazusa DNA Research Institute, Kisarazu (JP)

( * ) Notice: Subject to any disclaimer, the term of this patent is extended or adjusted under 35 U.S.C. 154(b) by 302 days.

This patent is subject to a terminal disclaimer.

(21) Appl. No.: 17/718,789

(22) Filed: Apr. 12, 2022

(65) Prior Publication Data
US 2023/0011813 A1    Jan. 12, 2023

Related U.S. Application Data

(63) Continuation of application No. 17/463,733, filed on Sep. 1, 2021, now abandoned, which is a continuation of application No. 17/148,832, filed on Jan. 14, 2021, now abandoned, which is a continuation of application No. 16/893,714, filed on Jun. 5, 2020, now abandoned, which is a continuation of application No. 16/663,799, filed on Oct. 25, 2019, now abandoned, which is a continuation of application No. 16/357,772, filed on Mar. 19, 2019, now abandoned, which is a continuation of application No. 15/554,890, filed as application No. PCT/JP2016/056453 on Mar. 2, 2016, now Pat. No. 10,280,202.

(30) Foreign Application Priority Data

Mar. 2, 2015    (JP) ................................ 2015-040368

(51) Int. Cl.
| | |
|---|---|
| C07K 14/415 | (2006.01) |
| A23L 11/00 | (2021.01) |
| A23L 33/00 | (2016.01) |
| A23L 33/10 | (2016.01) |
| A23L 33/17 | (2016.01) |
| A61K 38/00 | (2006.01) |
| C07K 7/06 | (2006.01) |

(52) U.S. Cl.
CPC ............ *C07K 14/415* (2013.01); *A23L 11/00* (2016.08); *A23L 33/10* (2016.08); *A23L 33/17* (2016.08); *A23L 33/30* (2016.08); *A23L 33/40* (2016.08); *A61K 38/00* (2013.01); *C07K 7/06* (2013.01); *A23V 2002/00* (2013.01)

(58) Field of Classification Search
CPC ......... C07K 14/415; C07K 7/06; A23L 11/00; A23L 33/10; A23L 33/17; A23L 33/30; A23L 33/40; A61K 38/00; A23V 2002/00
See application file for complete search history.

(56) References Cited

U.S. PATENT DOCUMENTS

| | | |
|---|---|---|
| 10,280,202 B2 | 5/2019 | Ohinata et al. |
| 2004/0137558 A1 | 7/2004 | Yokozeki et al. |
| 2010/0210564 A1 | 8/2010 | Ohinata et al. |

FOREIGN PATENT DOCUMENTS

| | | |
|---|---|---|
| EP | 2130533 A1 | 12/2009 |
| EP | 2557088 A1 | 2/2013 |
| JP | 2007-091656 A | 4/2007 |
| JP | 2009-247270 A | 10/2009 |
| JP | 2010-222300 A | 10/2010 |
| JP | 2014-162735 A | 9/2014 |
| WO | 2016140277 A1 | 9/2016 |

OTHER PUBLICATIONS

International Search Report dated Mar. 29, 2016 from International Application No. PCT/JP2016/056453, 4 pages, including English translation.
Extended European Search Report dated Jul. 24, 2018 from European Application No. 16758970.4.
Hatakeyma et al., "Modulating Effects of Soy Protein Isolate and Soy Protein Hydrolysate on Human Brain Function", Daizu Tanpakushitsu Kenkyu (Soy Protein Research, Japan) 2003, vol. 6, pp. 147-152 with English Abstract.
Mori et al., "Characterization of soy-deprestatin, a novel orally-active decapeptide that exerts antidepressant-like effects via gut-brain communication," The FASEB Journal, 2017 (published online), pp. 1-14.
Nishi et al., "The soybean β-conglycinin β 51-63 fragment supresses appetite by stimulating cholecystokinin release in rats," The Journal of Nutrition, 2003, pp. 2537-2542.
Ota et al., "Rational identification of a novel soy-derived anxiolytic-like undecapeptide acting via gut-brain axis after oral administration," Neurochemistry International, 2017, vol. 15, pp. 51-57.
Otsuka et.al., "Tanjitsu Joken ni Okeru Mouse no Jodo Kanren Kodo no Eiyogakuteki Seigyo", Journal of Pet Nutrition, 2014, vol. 17, Dai 16 Kai Taikaigo, pp. 54-55 and English summary.
The Ministry of Agriculture, Forestry and Fisheries of Japan Research Council Jimukyoku, "Nippon-gata Shokuhin Sozai Seibun no No Kino Chosetsu Koka no Kaiseki, Shokuhin no Anzensei Oyobi Kinosei ni Kansuru Kenkyu-Kinosei", 2008, No. 446, pp. 352-361 and English summary.
Yoshikawa, "Bioactive peptides derived from natural proteins with respect to diversity of their receptors and physiological effects," Peptides, 2015, vol. 72, pp. 208-225.

*Primary Examiner* — Olga N Chernyshev
(74) *Attorney, Agent, or Firm* — Goodwin Procter LLP

(57) ABSTRACT

This invention provides a peptide consisting of (i) the amino acid sequence LSSTOAOOSY (SEQ ID NO: 1), (ii) the amino acid sequence LSSTOAQQSW (SEQ ID NO: 6), or (iii) the amino acid sequence LSSTOAQQSF (SEQ ID NO: 7).

19 Claims, 8 Drawing Sheets
Specification includes a Sequence Listing.

Tail suspension test

Forced swim test

Elevated plus-maze test

Open field test

SEQUENCE LISTING

<160> NUMBER OF SEQ ID NOS: 8

<210> SEQ ID NO 1
<211> LENGTH: 10
<212> TYPE: PRT
<213> ORGANISM: Artificial Sequence
<220> FEATURE:
<223> OTHER INFORMATION: Designed peptide

<400> SEQUENCE: 1

Leu Ser Ser Thr Gln Ala Gln Gln Ser Tyr
1               5                   10

<210> SEQ ID NO 2
<211> LENGTH: 9
<212> TYPE: PRT
<213> ORGANISM: Artificial Sequence
<220> FEATURE:
<223> OTHER INFORMATION: Designed peptide

<400> SEQUENCE: 2

Leu Ser Ser Thr Gln Ala Gln Gln Ser
1               5

<210> SEQ ID NO 3
<211> LENGTH: 9
<212> TYPE: PRT
<213> ORGANISM: Artificial Sequence
<220> FEATURE:
<223> OTHER INFORMATION: Designed peptide

<400> SEQUENCE: 3

Ser Ser Thr Gln Ala Gln Gln Ser Tyr
1               5

<210> SEQ ID NO 4
<211> LENGTH: 5
<212> TYPE: PRT
<213> ORGANISM: Artificial Sequence
<220> FEATURE:
<223> OTHER INFORMATION: Designed peptide

<400> SEQUENCE: 4

Leu Ser Ser Thr Gln
1               5

<210> SEQ ID NO 5
<211> LENGTH: 5
<212> TYPE: PRT
<213> ORGANISM: Artificial Sequence
<220> FEATURE:
<223> OTHER INFORMATION: Designed peptide

<400> SEQUENCE: 5

Ala Gln Gln Ser Tyr
1               5

<210> SEQ ID NO 6
<211> LENGTH: 10
<212> TYPE: PRT
<213> ORGANISM: Artificial Sequence
<220> FEATURE:
<223> OTHER INFORMATION: Designed peptide

<400> SEQUENCE: 6

Leu Ser Ser Thr Gln Ala Gln Gln Ser Trp
1               5                   10

```
<210> SEQ ID NO 7
<211> LENGTH: 10
<212> TYPE: PRT
<213> ORGANISM: Artificial Sequence
<220> FEATURE:
<223> OTHER INFORMATION: Designed peptide

<400> SEQUENCE: 7

Leu Ser Ser Thr Gln Ala Gln Gln Ser Phe
1               5                   10

<210> SEQ ID NO 8
<211> LENGTH: 10
<212> TYPE: PRT
<213> ORGANISM: Artificial Sequence
<220> FEATURE:
<223> OTHER INFORMATION: Designed peptide
<220> FEATURE:
<221> NAME/KEY: MOD_RES
<222> LOCATION: (10)..(10)
<223> OTHER INFORMATION: AMIDATION

<400> SEQUENCE: 8

Leu Ser Ser Thr Gln Ala Gln Gln Ser Tyr
1               5                   10
```

PEPTIDE

CROSS-REFERENCE TO RELATED APPLICATIONS

The present application is a continuation of U.S. application Ser. No. 17/463,733, filed Sep. 1, 2021 (the contents of which are incorporated herein by reference in their entirety), which is a continuation of U.S. application Ser. No. 17/148,832, filed Jan. 14, 2021, now abandoned, which is a continuation of U.S. application Ser. No. 16/893,714, filed Jun. 5, 2020, now abandoned, which is a continuation of U.S. application Ser. No. 16/663,799, filed Oct. 25, 2019, now abandoned, which is a continuation of U.S. application Ser. No. 16/357,772, filed Mar. 19, 2019, now abandoned, which is a continuation of U.S. application Ser. No. 15/554,890, now U.S. Pat. No. 10,280,202, issued May 7, 2019, which is a U.S. National Stage application of PCT/JP2016/056453, filed Mar. 2, 2016, which claims priority to the specification of Japan Patent Application No. 2015-040368 (the entire disclosure of which is incorporated in the present specification by reference) filed on Mar. 2, 2015.

TECHNICAL FIELD

Sequence Listing

The present application contains a Sequence Listing which has been submitted electronically in ASCII format and is hereby incorporated by reference in its entirety. Said ASCII copy, created Nov. 21, 2024, is named DGS-001C6_Sequence_Listing_ST25.txt and is 2,106 bytes in size.

The present invention relates to a novel peptide. The present invention also relates to a pharmaceutical and a food product comprising the peptide.

Background Art

Japan is facing a super-aged society where one in four people is elderly. In such a super-aged society, realization of a vibrant society of health and longevity is desired. Elderly people, however, have problems of reduced neurological function, such as diminished motivation, increased stress, and decreased appetite.

Soft food products that deal with a reduction in swallowing and/or masticatory function have been developed in the field of nursing care food products. In the future, there will be a need for developing next-generation nursing care food products with functionality that can ameliorate the above-described reduced neurological function.

PTL 1 discloses a wheat-gluten-derived peptide that exhibits antidepressant activity. However, there are no known peptides that can ameliorate diminished motivation.

CITATION LIST

Patent Literature

PTL 1: JP2014-162735A

SUMMARY OF INVENTION

Technical Problem

An object of the present invention is to provide a novel peptide having an ameliorating effect on diminished motivation, depression, or mood disorder, and a pharmaceutical and a food product comprising the peptide.

Solution to Problem

The present inventors conducted extensive research to achieve the above object and succeeded in isolating a novel peptide having an ameliorating effect on diminished motivation, depression, or mood disorder. The present inventors further conducted research based on this finding and accomplished the present invention.

More specifically, the present invention includes the following embodiments.

Item 1. A peptide consisting of
(i) the amino acid sequence LSSTQAQQSY (SEQ ID NO: 1),
(ii) the amino acid sequence LSSTQAQQSW (SEQ ID NO: 6), or
(iii) the amino acid sequence LSSTQAQQSF (SEQ ID NO: 7).

Item 2. A peptide consisting of the amino acid sequence LSSTQAQQSY (SEQ ID NO: 1), the peptide being derived from a thermolysin digest of soybean β-conglycinin protein.

Item 3. A pharmaceutical composition comprising the peptide according to Item 1 or 2 as an active ingredient.

Item 4. The pharmaceutical composition according to Item 3, which is a drug for treating diminished motivation, an antidepressant drug, or a drug for treating mood disorder or a symptom caused thereby.

Item 5. A food product comprising the peptide according to Item 1 or 2.

Item 6. A food product characterized in that the peptide according to Item 1 or 2 is added to the food product.

Item 7. The food product according to Item 5 or 6 for ameliorating diminished motivation, depression, or mood disorder, or a condition caused thereby.

Item 8. A method for ameliorating or treating diminished motivation, depression, or mood disorder, or a symptom caused thereby, the method comprising administering the peptide according to Item 1 or 2 to a patient suffering from diminished motivation, depression, or mood disorder, or a symptom caused thereby, or a subject at risk thereof.

Item 9. Use of the peptide according to Item 1 or 2 for ameliorating diminished motivation, depression, or mood disorder, or a symptom caused thereby.

Advantageous Effects of Invention

The pharmaceutical composition and the food product that contain the peptide of the present invention as an active ingredient have a high antidepressant effect/motivation enhancement effect with few side effects and are suitable for long-term use. Moreover, the pharmaceutical composition and the food product of the present invention are effective by oral administration.

Furthermore, natural short-chain peptides can be ingested as food; therefore, when ingested as food by individuals who are not ill but who have a problem of diminished motivation, such peptides can be expected to prevent diseases in such individuals.

The peptide of the present invention is an enzymatic digest of soybean β-conglycinin protein and is thus free of side effects. In addition, soybean β-conglycinin protein, which is abundant in soybeans, can be produced at low cost.

BRIEF DESCRIPTION OF DRAWINGS

FIG. 12 shows the sequence of a peptide LSSTQAQQSY (SEQ ID NO: 1).

DESCRIPTION OF EMBODIMENTS

Figure 1A:
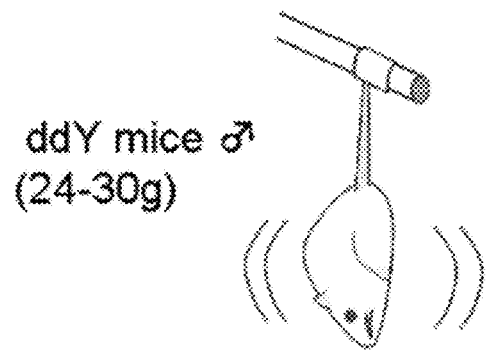
FIG. 1A shows a method for the tail suspension test. As test animals, 24- to 30-g male ddY mice were used.

The peptide of the present invention is a peptide of 10 residues, the peptide consisting of (i) LSSTQAQQSY (SEQ ID NO: 1), (ii) the amino acid sequence LSSTQAQQSW (SEQ ID NO: 6), or (iii) the amino acid sequence LSSTQAQQSF (SEQ ID NO: 7).

Each of the amino acids forming the peptide may be an L-amino acid, D-amino acid, or DL-amino acid (the mixture of D-amino acid and L-amino acid, including both a racemic amino acid and an amino acid containing an excess of either one of the enantiomers). Preferably, the peptide contains only L-amino acids or only D-amino acids. Particularly, a peptide containing only L-amino acids is preferred.

When the peptide used in the present invention has two or more asymmetric carbons, its enantiomer, diastereomer(s), or a mixture thereof in any ratio may also be used. Separation of the enantiomer or diastereomer may be performed using a general column, for example, using a chiral column, by a method in which the enantiomer or diastereomer is optically resolved in the form of a derivative by introducing an optically active group, and the optically active group is subsequently removed; a method in which the enantiomer or diastereomer is optically resolved by forming a salt with an optically active acid or base; or any other known method.

The peptide may have one or more modifications. The amino terminus (N-terminus) of the peptide may have a modification, such as a free amino group ($NH_2$—) or an acetyl group ($CH_3CO$—). The carboxy terminus (C-terminus) of the peptide may have a modification, such as a free carboxy group (—COOH) or an amide group. The amino acid residues of the peptide may be unmodified or have a modification, such as a phosphate group or a sugar chain.

The peptide of the present invention may be in the form of a salt (acid addition salt or base salt). Examples of acid addition salts include salts with inorganic acids, such as hydrochloric acid, sulfuric acid, nitric acid, phosphoric acid, hydrobromic acid, and perchloric acid; and salts with organic acids, such as citric acid, succinic acid, maleic acid, fumaric acid, malic acid, tartaric acid, p-toluenesulfonic acid, benzenesulfonic acid, methanesulfonic acid, and trifluoroacetic acid. Examples of base salts include salts with alkali metals, such as sodium, potassium, and lithium; salts with alkaline earth metals, such as calcium and magnesium; and the like.

The peptide of the present invention may be in the form of a solvate. Examples of solvates include solvates with water (hydrates), methanol, ethanol, isopropanol, acetic acid, tetrahydrofuran, acetone, dimethylformamide, dimethyl sulfoxide, dimethylacetamide, acetamide, ethylene glycol, propylene glycol, dimethoxyethane, and the like.

The peptide of the present invention, in particular the peptide consisting of the amino acid sequence LSSTQAQQSY (SEQ ID NO: 1), can be obtained by hydrolyzing β-conglycinin (β-CG) protein, which is a major storage protein of soybeans, using thermolysin.

Thermolysin is a known proteolytic enzyme (protease) derived from thermostable bacterium *Bacillus thermoproteolyticus* (EC3.4.24.4). Thermolysin can be used as a food additive in Japan. As thermolysin, commercially available thermolysin of, for example, reagent grade or food additive grade may be used.

The substrate to be hydrolyzed with thermolysin is not particularly limited as long as it contains soybean β-CG protein. Examples include the soybean itself, pomace obtained by extracting soybean oil from soybeans (also called meal or defatted soybean), purified β-conglycinin protein, and the like.

The hydrolysis using thermolysin is performed under conditions such that a peptide consisting of 10 amino acid residues is obtained. The reaction temperature can suitably be selected from, for example, 30 to 70° C., 30 to 40° C., 40 to 70° C., or 50 to 65° C. The reaction time can be suitably selected from, for example, about 30 minutes to 48 hours, about 1 to 10 hours, or about 2 to 8 hours. The pH at which the reaction is carried out can be suitably selected from the pH range of about 6.5 to 8.5 or about 7 to 8. In one preferred embodiment, the reaction can be performed for about 2 to 8 hours under the following conditions: a temperature of about 30 to 40° C. and a pH of 6.5 to 8.5 (in particular, about pH 7.5).

The peptide of the present invention may not be obtained under conditions such that hydrolysis is excessively performed.

If necessary, thermolysin is deactivated by heating at a temperature at which thermolysin is deactivated (for example, heating at a temperature exceeding 80° C. for about 5 to 60 minutes).

The hydrolysis product may be used as it is, or purified to separate the active ingredient peptide that is to be used.

The peptide of the present invention can also be obtained by a peptide synthesis method. Specifically, a solution-phase method or a solid-phase method is generally used in peptide synthesis. Among these, a starting material having a reactive carboxy group can be condensed with a starting material having a reactive amino group by a method via an active ester using HBTU, etc. or by a method using a coupling agent, such as carbodiimide. When the resulting condensation product has a protecting group, the peptide can also be produced by removing the protecting group.

Functional groups that should not be involved in the reaction of this reaction step are protected with protecting groups. Examples of amino-protecting groups include benzyloxycarbonyl (CBZ), t-butyloxycarbonyl (Boc), 9-fluorenylmethyloxycarbonyl (Fmoc), and the like. Examples of carboxy-protecting groups include groups capable of forming alkyl esters, benzyl esters, and the like. In the case of a solid-phase method, the C-terminal carboxy group is bonded to a support, such as chlorotrityl resin, chloromethyl resin, oxymethyl resin, or p-alkoxybenzyl alcohol resin. The condensation reaction is carried out in the presence of a condensing agent, such as carbodiimide, or using an N-protecting amino acid active ester or a peptide active ester.

The protecting group is removed after the completion of the condensation reaction. In the case of a solid-phase method, the bond between the C-terminus of the peptide and the resin is also cleaved. Furthermore, the peptide of the present invention is purified according to a general method. Examples of purification methods include ion-exchange chromatography, reverse-phase liquid chromatography, affinity chromatography, and the like. The synthesized peptide is analyzed by the Edman degradation technique, using a protein sequencer, GC-MS, or the like that reads an amino acid sequence from the C-terminus.

The peptide of the present invention can also be synthesized according to an enzymatic method (see WO2003/010307).

The peptide of the present invention is effective in ameliorating or treating diminished motivation, depression, or mood disorder, or conditions (symptoms) caused thereby. The phrases "diminished motivation" and "mood disorder" as used herein include impulses of mind (spirit), such as feeling unmotivated and having no interest or concern in anything. "Diminished motivation" and "mood disorder" are not limited to diseases or conditions resulting from depression, and also include aging (senescence), stress (e.g., adjustment disorder), and like conditions of those who are not diagnosed with depression.

The effect of treating or ameliorating diminished motivation (which can be rephrased as "motivation enhancement effect") can be evaluated, for example, using as an index a reduction in the immobility time in the tail suspension test or the forced swim test, both of which are used for evaluating therapeutic antidepressant drugs in mice.

The peptide of the present invention also has an anxiolytic effect and is also effective in ameliorating or treating anxiety. The anxiolytic effect can be evaluated by, for example, the elevated plus-maze test or the open field test. Depression is caused by the following vicious cycle: first, stress is caused, one feels that there is no support from those around him or her, brain dysfunction occurs, the way of seeing things become negative, and then he or she overestimates the burden and feels more stress (see page 14 of *Chiryo Gaidorain II Daiutsubyosei Shogai* (Treatment Guideline II Major Depressive Disorder) by the Japanese Society of Mood Disorders). The peptide of the present invention, which exhibits an antistress effect, can be expected to remove causes of diminished motivation, depression, or mood disorder, or conditions (symptoms) caused thereby.

The peptide of the present invention can be provided as a pharmaceutical composition or a food product (food composition).

The route of administration of the peptide of the present invention or a product containing the peptide of the present invention is not particularly limited. The peptide or the product can be administered orally, parenterally, or intrarectally. The peptide or the product can be administered orally or non-orally. Among these, oral administration is preferable because the obtained effect is high.

The dose of the peptide varies depending on the type of compound, the mode of administration, and the condition, age, and the like of an individual to whom the peptide is administered. The daily dose for an adult is typically 0.01 to 500 mg/kg, preferably 0.05 to 100 mg/kg, and more preferably 0.1 to 30 mg/kg. The peptide (active ingredient) of the present invention is typically administered in the form of a pharmaceutical composition prepared by mixing with one or more pharmaceutical carriers. A pharmaceutical carrier that is commonly used in the field of pharmaceutical preparations and that does not react with the peptide of the present invention is used.

The peptide of the present invention can be used by itself as a pharmaceutical or a food product, or can be used singly or in a combination with suitable nontoxic carriers for oral administration, diluents, or excipients to make food preparations or pharmaceutical preparations such as tablets (uncoated tablets, sugar-coated tablets, effervescent tablets, film-coated tablets, chewable tablets, and the like), capsules, troches, powders, fine granules, granules, solutions, suspensions, emulsions, pastes, creams, injections (including infusions such as amino acid infusions and electrolyte infusions), and sustained-release preparations including enteric-coated tablets, capsules, and granules. The amount of the peptide in the food product can be suitably selected and is typically in the range of 0.01 to 100 wt %.

Specific examples of pharmaceutical carriers or carriers for oral administration, diluents, excipients, and like substances that can be added to the pharmaceutical or the food product include lactose, glucose, mannite, dextrin, cyclodextrin, starch, sucrose, magnesium aluminometasilicate, synthetic aluminum silicate, sodium carboxymethyl cellulose, hydroxypropyl starch, calcium carboxymethyl cellulose, ion exchange resins, methylcellulose, gelatin, gum arabic, hydroxypropylcellulose, hydroxypropylmethylcellulose, polyvinylpyrrolidone, polyvinyl alcohol, light anhydrous silicic acid, magnesium stearate, talc, tragacanth, bentonite, veegum, titanium oxide, sorbitan fatty acid esters, sodium lauryl sulfate, glycerin, fatty acid glycerol esters, purified lanolin, glycerogelatin, polysorbate, macrogol, vegetable oils, waxes, liquid paraffin, white petrolatum, fluorocarbon, nonionic surfactants, propylene glycol, water, and the like.

Examples of the dosage form include tablets, capsules, granules, powders, syrups, suspensions, suppositories, ointments, creams, gels, patches, inhalants, injections, and the like. These preparations are prepared according to general methods. Liquid preparations may be dissolved or suspended in water or other suitable solvents prior to use. Tablets and granules may be coated using known methods. Injections are prepared by dissolving the peptide of the present invention in water. As required, injections may also be prepared by dissolving the peptide in physiological saline or a glucose solution, or may additionally contain buffers or preservatives.

These preparations may contain the peptide of the present invention in an amount of 0.01 to 100 wt %, and preferably 1 to 90 wt %. These preparations may also contain other therapeutically beneficial ingredients.

Solid preparations for oral administration may be prepared by mixing the active ingredient with excipients, such as lactose, starch, crystalline cellulose, calcium lactate, and silicic acid anhydride, to form powders. Further, if necessary, for example, binders, such as saccharose, hydroxypropylcellulose, and polyvinylpyrrolidone; and disintegrators, such as carboxymethyl cellulose and calcium carboxymethyl cellulose, may also be added and the resulting mixtures are dry- or wet-granulated to form granules. Tablets may be prepared by tableting these powders or granules as they are, or after adding lubricants, such as magnesium stearate and talc, thereto. These granules or tablets can be coated with enteric coating bases, such as hydroxypropylmethylcellulose phthalate and methacrylic acid-methyl methacrylate polymer, to form enteric-coated preparations; or coated with, for example, ethylcellulose, carnauba wax, or hydrogenated oil to form sustained-release preparations. Capsules may be prepared by filling hard capsules with powders or granules, or by coating with gelatin films the active ingredient as it is, or after being dissolved in glycerin, polyethylene glycol, sesame oil, olive oil, or the like to form soft capsules.

Liquid preparations for oral administration may be prepared by dissolving in water the active ingredient together with sweetening agents, such as saccharose, sorbitol, and glycerin, to form transparent syrups; by further adding essential oils, ethanol, etc., thereto to form elixirs; or by further adding gum arabic, tragacanth, polysorbate 80, sodium carboxymethyl cellulose, etc., thereto to form emulsions or suspensions. These liquid preparations may optionally contain taste-improving agents, coloring agents, preservatives, etc.

Specific examples of forms of food products that can be prepared by adding or blending the peptide of the present invention include beverages (such as coffee, cocoa, juices, soft drinks, mineral drinks, tea beverages, green tea, black tea, oolong tea, milk beverages, lactic acid bacteria beverages, yoghurt beverages, carbonated beverages, and like nonalcoholic drinks, and alcoholic drinks), confectioneries (such as hard candies, gum, gummi candies, jellies, pudding, mousses, cakes, candies, cookies, crackers, biscuits, chocolate, and ice confectioneries (for example, ice creams, popsicles, sherbets, and shaved ice)), seasoned powder to be sprinkled over rice, dressings, seasonings, processed-soybean products (for example, bean curd, miso, soy sauce, yuba (bean curd sheet), soybean flour, and fermented soybeans), processed meat products (for example, hamburger steaks, meat loaf, meatballs, and tsukune (meat formed into bite-sized balls)), processed fish meat products (for example, kamaboko (steamed fish paste) and chikuwa (a kind of fish paste)), retort foods, jelly-like foods (for example, jellies, agar, and jelly-like beverages), and the like. Food products that can be prepared by adding or blending the peptide of the present invention may take the form of health foods, functional foods, nutritional supplements, dietary supplements, foods for specified health uses, foods for the ill/combined foods for the ill (a category of foods for special dietary uses, approved by Japan's Ministry of Health, Labour and Welfare), and foods for the elderly (a category of foods for special dietary uses, approved by Japan's Ministry of Health, Labour and Welfare). These foods may be in the form of uncoated tablets, film-coated tablets, sugar-coated tablets granules, powders, tablets, capsules (including both hard and soft capsules), chewable forms, syrups, drinks, and the like. The preparation of food products obtained by adding or blending the peptide of the present invention can be performed according to known methods.

EXAMPLES

The present invention is described in more detail below with reference to Examples. The Examples, however, do not limit the scope of the invention.

Methods

Tail Suspension Test

Figure 2:
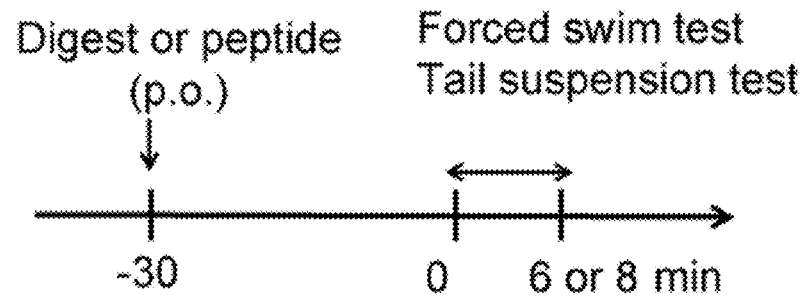
FIG. 2 shows methods for the tail suspension test and the forced swim test. The tests were performed 30 minutes after oral administration (per os (p.o.)) of a test substance (enzymatic digest or peptide). In the tail suspension test, the immobility time during the period from 0 to 6 minutes was measured, and in the forced swim test, the immobility time during the period from 0 to 8 minutes was measured.

As shown in FIG. 1A, each mouse (ddY mice, male, 24 to 30 g) was suspended by its tail, and the amount of time for the mouse to lose motivation and become immobile after initially showing escape behaviors (immobility time) was measured. The test was carried out (0 minutes) 30 minutes after administration of a test substance, and the immobility time during the period from 0 to 6 minutes was measured (FIG. 2).

When an antidepressant drug, such as imipramine, is administered, the immobility time is reduced. Thus, when a reduction in the immobility time is observed, it can be evaluated that the test substance has an antidepressant-like effect. Immobility is considered a despair state; therefore, a reduction in the immobility time also serves as an index for improvement of a despair state, i.e., enhancement of motivation.

Forced Swim Test

Figure 1B:
FIG. 1B shows a method for the forced swim test.

As shown in FIG. 1B, each mouse (ddY mice, male, 24 to 30 g) was placed in an inescapable water bath and forced to swim, and the amount of time for the mouse to lose motivation and become immobile after initially showing escape behaviors (immobility time) was measured. The test was carried out (0 minutes) 30 minutes after administration of a test substance, and the immobility time during the period from 0 to 8 minutes was measured (FIG. 2).

As in the tail suspension test, when an antidepressant drug, such as imipramine, is administered, the immobility time is reduced. Thus, when a reduction in the immobility time is observed, it can be evaluated that the test substance has an antidepressant-like effect. Immobility is considered a despair state; therefore, a reduction in the immobility time also serves as an index for improvement of a despair state, i.e., enhancement of motivation.

Elevated Plus-Maze Test (EPM)

Figure 3A:
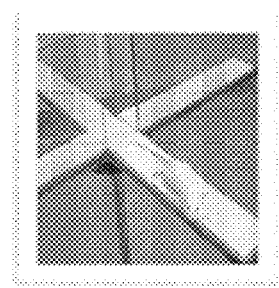
FIG. 3A shows a method for the elevated plus-maze test (EPM)

The elevated plus-maze includes two open arms (25×5 cm) and two closed arms (25×5×15 cm), which are joined to a central platform 50 cm high above the floor (see FIG. 3A). Because the closed arms are surrounded by walls, a mouse can safely walk in the closed arms in spite of the elevated position. On the other hand, because the open arms are not surrounded by walls, a mouse walking along the open arms feels anxious that it may fall from the elevated position. Thus, the more time the mouse spends in the open arms, or the greater the number of entries into the open arms, the less anxious the mouse feels. Thus, the anxiolytic activity is determined based on these indices.

Figure 4:
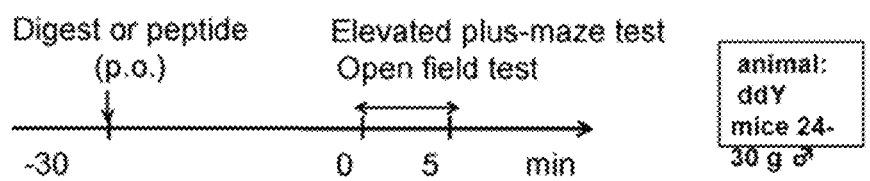
FIG. 4 shows methods for the elevated plus-maze test and the open field test. The tests were performed 30 minutes after oral administration (per os (p.o.)) of a test substance (enzymatic digest or peptide), and evaluation was performed for a 5-minute test period. As test animals, 24- to 30-g male ddY mice were used.

As shown in FIG. 4, a test substance was administered to mice (ddY mice, male, 24 to 30 g) 30 minutes before testing. Each mouse was placed on a portion of the central platform facing one of the open arms 30 minutes after the administration, and the test was started. During the 5-minute test time, the cumulative time spent in the open arms (time in open arms), the number of visits to the open arms (visit to open arms), and the total number of visits to any of the arms (total visits) were recorded. The percentage of time spent in the open arms and the percentage of the number of visits to the open arms were calculated as indices of anxiety.

Open Field Test

Figure 3B:
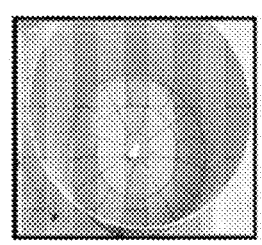
FIG. 3B shows a method for the open field test (OF).

Mice generally prefer the peripheral portion of a circle, and rarely exhibit exploratory behaviors into the center portion (see FIG. 3B). Similar to the case of the elevated plus-maze test, the higher the percentage of exploratory behaviors of a mouse in the center portion of a circle, the less anxious the mouse feels. Thus, the anxiolytic activity is determined based on this index.

As shown in FIG. 4, a test substance was administered to mice (ddY mice, male, 24 to 30 g) 30 minutes before testing. Each mouse was placed in an open field 30 minutes after the administration, and the test was started. The percentage of exploratory behaviors in the center portion of the circle (the time spent in the center circle (open field) (Time in 12 cm circle) and the percentage of the number of visits to the center circle (Visits in 12 cm circle)) during the 5-minute test time were evaluated.

Statistical Analysis

The data obtained from the tests were represented as the sum of the mean and the standard error of the mean (SEM). The data were analyzed by one-way or two-way ANOVA, followed by the Fisher test for multiple comparisons. The difference was considered significant when $p<0.05$ ("*" in the graphs) or when $p<0.01$ ("**" in the graphs).

Production Example

Enzymatic Digests

Purified β-conglycinin (β-CG) protein and a digestive enzyme were mixed at the weight ratio of enzyme: p-CG=1: 100 (final concentration of β-CG: 20 mg/mL), and a reaction was carried out in the attached buffer.

The enzymes used and reaction conditions were as follows:
(i) thermolysin (Seikagaku Corporation); reaction temperature: 37° C., reaction time: 5 hours; reaction buffer: pH 7.5
(ii) subtilisin (Sigma); reaction temperature: 37° C., reaction time: 5 hours; reaction buffer: pH 7.5
(iii) sumizyme (Seikagaku Corporation); reaction temperature: 50° C., reaction time: 5 hours; reaction buffer: pH 7.0.

After the reaction times above, the samples were boiled (100° C., for 10 minutes) to stop the enzymatic reactions.

Peptides

The peptides LSSTQAQQSY (SEQ ID NO: 1), LSSTQAQQS (SEQ ID NO: 2), SSTQAQQSY (SEQ ID NO: 3), LSSTQ (SEQ ID NO: 4), and AQQSY (SEQ ID NO: 5) were synthesized by a standard method.

Experiments and Results

Example 1: Tail Suspension Test (Enzymatic Digests)

30 mg/kg of the thermolysin digest of β-CG, 30 mg/kg of the subtilisin digest of β-CG, and 30 mg/kg of the sumizyme digest of β-CG were used as test substances. The tail suspension test was performed using mice to which each test substance was individually orally administered (n=16-20). Administration of only physiological saline, which is a solvent, was performed as a control (the same applies hereinafter).

Figure 5A:
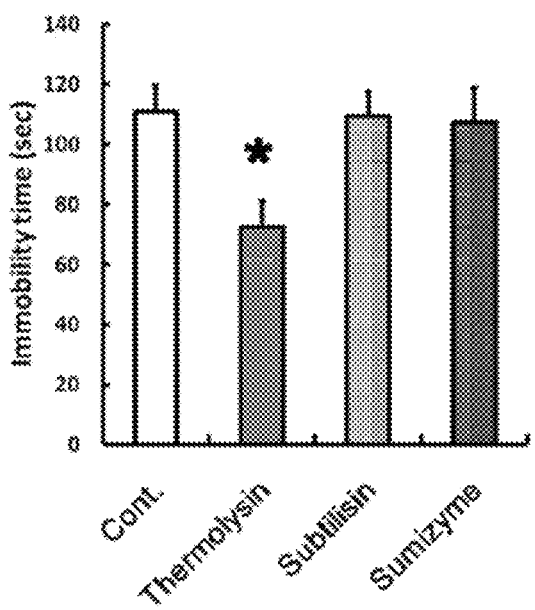
FIGS. 5A-B show the results of the tail suspension test in mice to which each enzymatic digest was individually orally administered.

FIG. 5A shows the results. A reduction in the immobility time was observed in only the case of using the thermolysin digest, among the three digests, compared with the control.

Example 2: Tail Suspension Test (Enzymatic Digest)

The tail suspension test was performed using mice to which 10 mg/kg or 30 mg/kg of the thermolysin digest of β-CG was orally administered as a test substance (n=11-12).

Figure 5B:
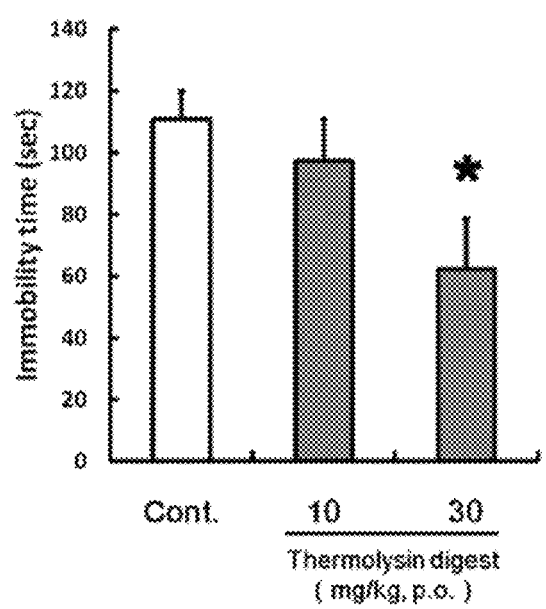

FIG. 5B shows the results. A reduction in the immobility time depending on the concentration of the thermolysin digest was observed.

Example 3: Forced Swim Test (Enzymatic Digest)

The forced swim test was performed using mice to which 30 mg/kg or 100 mg/kg of the thermolysin digest of β-CG was administered as a test substance (n=6).

Figure 6:
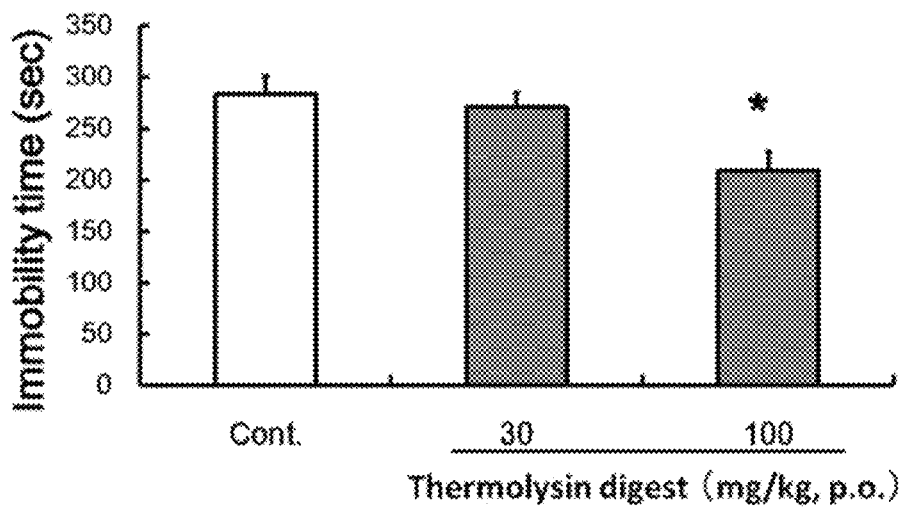
FIG. 6 shows the results of the forced swim test in mice to which an enzymatic digest was orally administered.

FIG. 6 shows the results. A reduction in the immobility time was observed when 100 mg/kg of the digest was orally administered.

Example 4: Tail Suspension Test (Peptide)

The tail suspension test was performed using mice to which 0.1 mg/kg, 0.3 mg/kg, 1 mg/kg, or 3 mg/kg of the peptide LSSTQAQQSY (SEQ ID NO: 1) was administered as a test substance (n=8-10).

Figure 7:
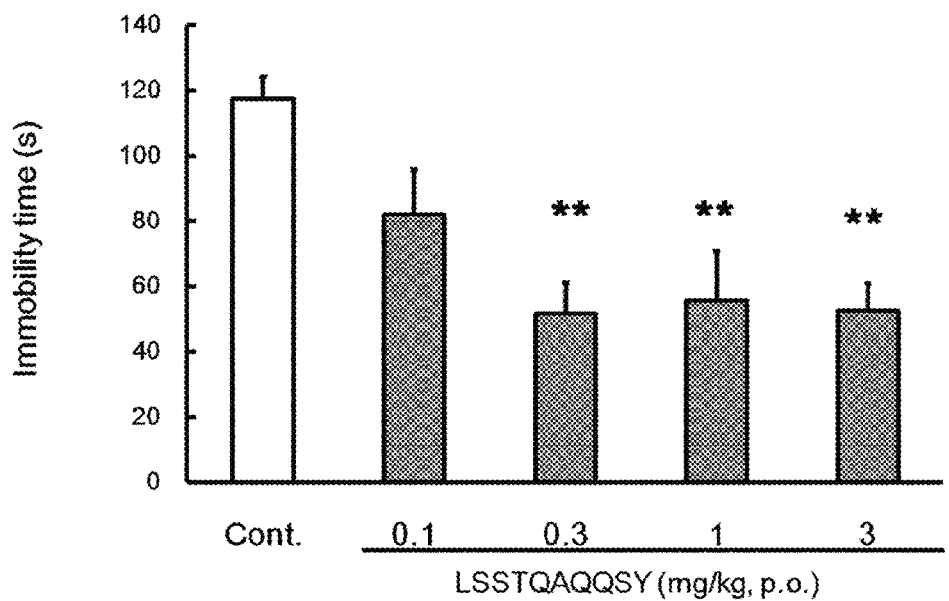
FIG. 7 shows the results of the tail suspension test in mice to which a peptide (LSSTQAQQSY (SEQ ID NO: 1)) was orally administered.

FIG. 7 shows the results. The immobility time was significantly reduced by orally administering the peptide in an amount of 0.3 mg/kg or more.

Example 5: Forced Swim Test (Peptide)

The forced swim test was performed using mice to which 0.3 mg/kg or 1 mg/kg of the peptide LSSTQAQQSY (SEQ ID NO: 1) was administered as a test substance (n=12-13).

Figure 8:
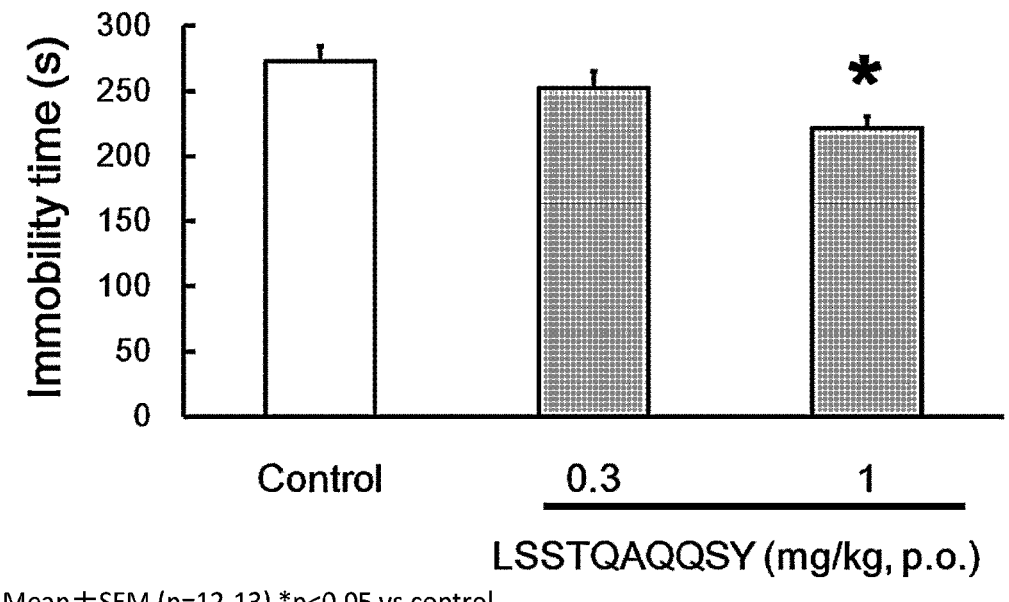
FIG. 8 shows the results of the forced swim test in mice to which a peptide (LSSTQAQQSY (SEQ ID NO: 1)) was orally administered.

FIG. 8 shows the results. The immobility time was significantly reduced by orally administering the peptide in an amount of 1 mg/kg or more.

Reference Example 1

The peptide LSSTQAQQSY (SEQ ID NO: 1) contained in the thermolysin digest of β-CG, the subtilisin digest of β-CG, and the sumizyme digest of β-CG was quantified by UPLC-ESI-MS.

The results showed that the thermolysin digest of β-CG contained the peptide LSSTQAQQSY (SEQ ID NO: 1) in an amount of 266 mg (21 mol %) per 100 g of the digest, whereas the peptide LSSTQAQQSY (SEQ ID NO: 1) was not detected in the subtilisin digest or the sumizyme digest.

This result and the results of Examples 1 to 5 revealed that the peptide LSSTQAQQSY (SEQ ID NO: 1), which the thermolysin digest of β-CG contains, exhibits an antidepressant effect (motivation enhancement effect).

Example 6: Structure-Activity Relationships of Peptides

The peptide LSSTQAQQS (SEQ ID NO: 2), which has a single residue deletion at the C-terminus of the peptide LSSTQAQQSY (SEQ ID NO: 1), the peptide SSTQAQQSY (SEQ ID NO: 3), which has a single residue deletion at the N-terminus of the peptide LSSTQAQQSY (SEQ ID NO: 1), the peptide LSSTQ (SEQ ID NO: 4), which consists of 5 residues that are the N-terminal half of the peptide LSSTQAQQSY (SEQ ID NO: 1), and the peptide AQQSY (SEQ ID NO: 5), which consists of 5 residues that are the C-terminal half of the peptide LSSTQAQQSY (SEQ ID NO: 1), were used as test substances. The tail suspension test was performed using mice to which 0.3 mg/kg of each test substance was individually orally administered (n=5-6 or 18-19).

Figure 9:
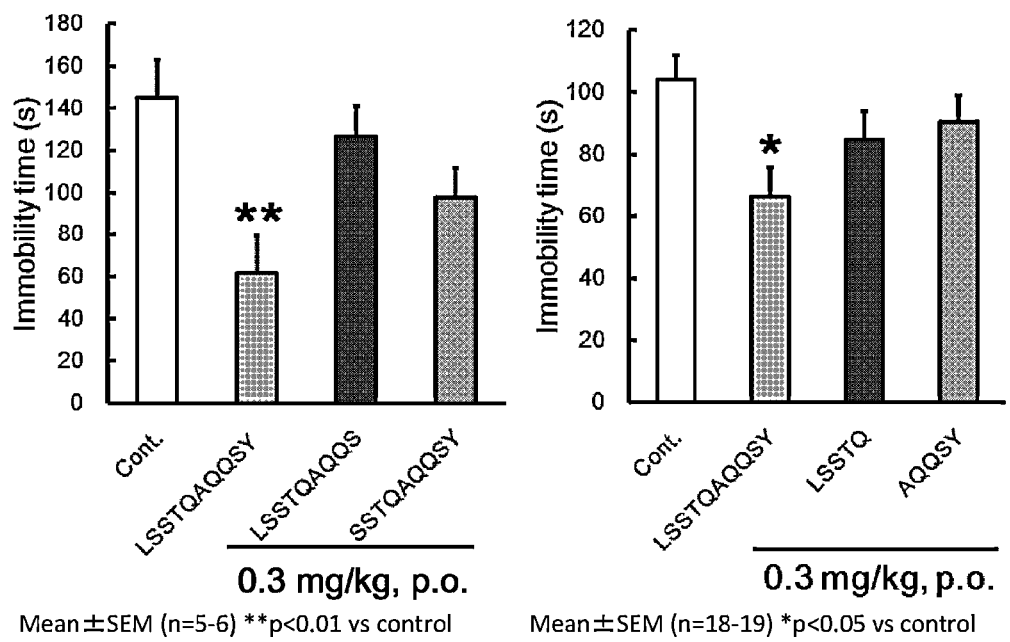
FIG. 9 shows the results of investigating the structure activity relationships of peptides (LSSTQAQQSY (SEQ ID NO: 1); LSSTQAQQS (SEQ ID NO: 2); SSTQAQQSY (SEQ ID NO: 3), LSSTQ (SEQ ID NO: 4), or AQQSY (SEQ ID NO: 5)) by the results of the tail suspension test.

FIG. 9 shows the results. No significant reduction in the immobility time was observed in any case compared with the case of using the peptide LSSTQAQQSY (SEQ ID NO: 1). This result revealed that not one of the N-terminal side and the C-terminal side of the peptide LSSTQAQQSY (SEQ ID NO: 1) alone is important, and that the full-length 10-residue peptide achieves the strongest immobility time reducing effect.

Example 7: Investigating the Mechanism of Action Using Antagonists (Enzymatic Digest)

The tail suspension test was performed using mice to which 30 mg/kg of the thermolysin digest of β-CG was orally administered (p.o.) in combination with each of the antagonists of various receptors. Three kinds of antagonists, i.e., WAY100135, which is an antagonist of the serotonin 5-HT1A receptor (dose: 10 mg/kg), SCH23390, which is an antagonist of the dopamine D1 receptor (dose: 30 μg/kg), and bicuculline, which is an antagonist of the GABA-A receptor (dose: 30 mg/kg), were used.

Figure 10:
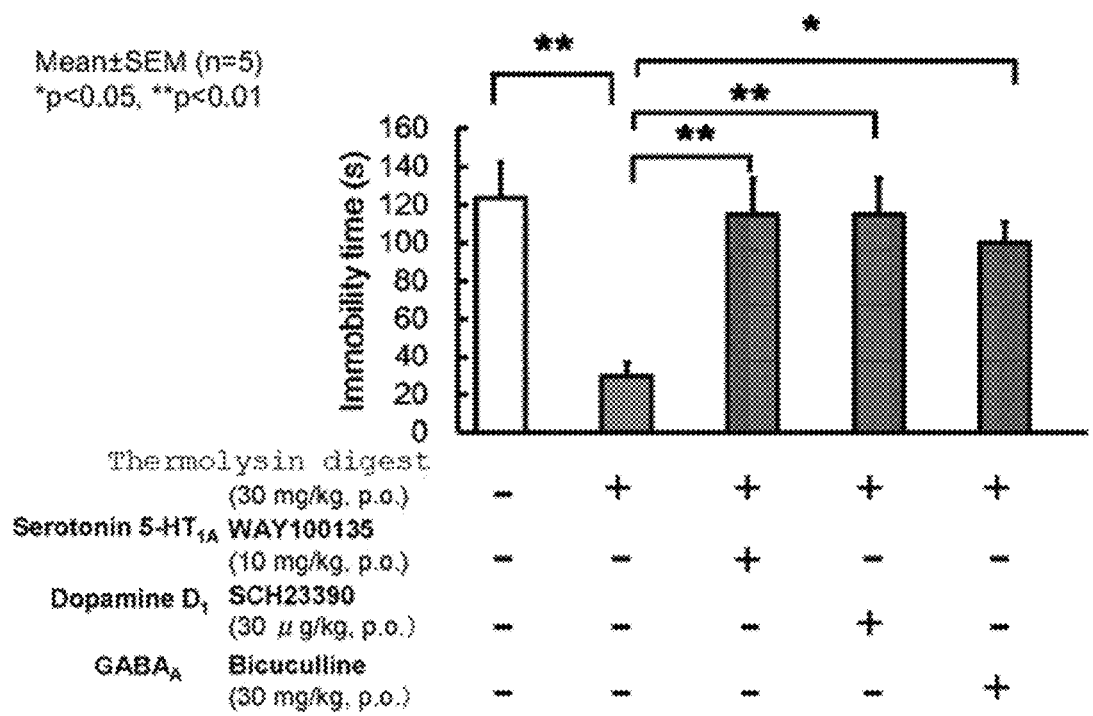
FIG. 10 shows the results of investigating the mechanism of action of enzymatic digests, using antagonists, by the results of the tail suspension test.

FIG. 10 shows the results. A reduction in the immobility time was significantly suppressed when the digest was used in combination with any of the inhibitors.

Example 8: Investigating the Mechanism of Action Using Antagonists (Peptide)

The tail suspension test was performed using mice to which 0.3 mg/kg of the peptide LSSTQAQQSY (SEQ ID NO: 1) was orally administered (p.o.) in combination with each of the antagonists of various receptors. Three kinds of antagonists, i.e., WAY100135, which is an antagonist of the serotonin 5-HT1A receptor (dose: 10 mg/kg), SCH23390, which is an antagonist of the dopamine D1 receptor (dose: 30 μg/kg), and bicuculline, which is an antagonist of the GABA-A receptor (dose: 30 mg/kg), were used.

Figure 11:
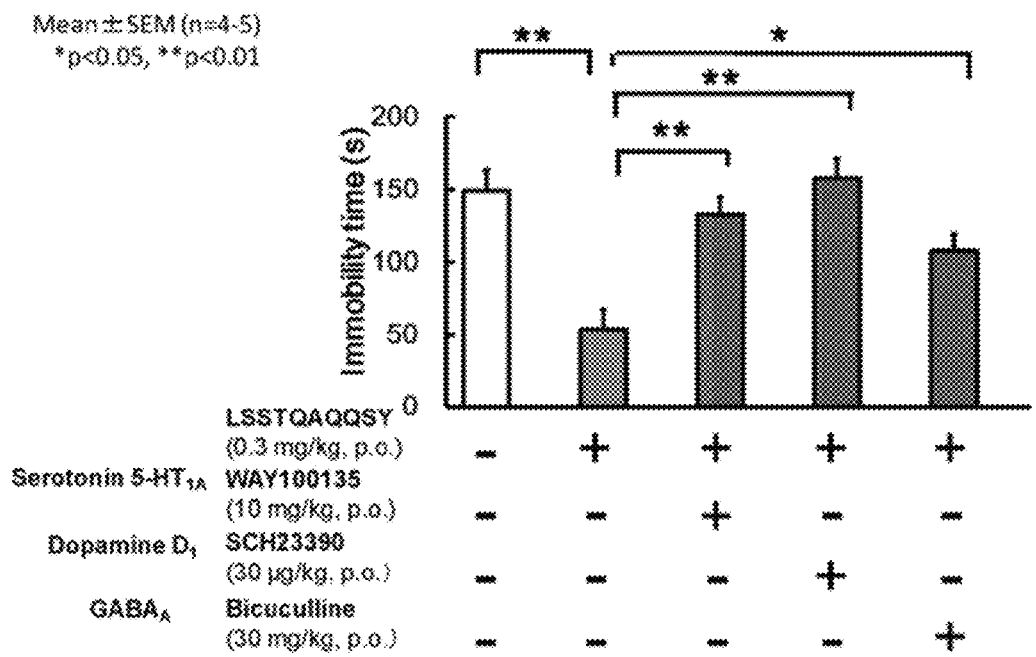
FIG. 11 shows the results of investigating the mechanism of action of peptides (LSSTQAQQSY (SEQ ID NO: 1)), using antagonists, by the results of the tail suspension test.

FIG. 11 shows the results. A reduction in the immobility time was significantly suppressed when the peptide was used in combination with any of the inhibitors.

Figure 12:
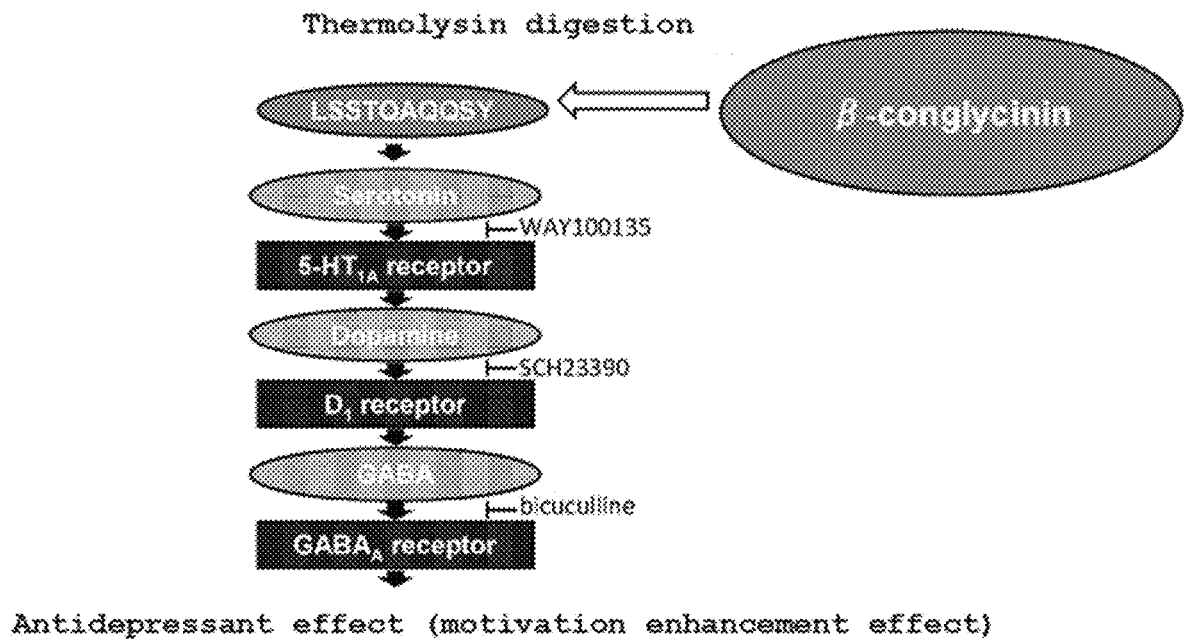
FIG. 12 shows an assumed model of the mechanism of action by which an antidepressant effect (motivation enhancement effect) is produced.

The results of Examples 7 and 8 suggested that the emotion regulation effect of the thermolysin digest of β-CG and the peptide LSSTQAQQSY (SEQ ID NO: 1) is via activation of serotonin 5-HT1A, dopamine D1, and GABAA receptors. FIG. 12 shows an assumed pathway of action.

Example 9: Elevated Plus-Maze Test (Enzymatic Digest)

The elevated plus-maze test was performed using mice to which 3 mg/kg, 10 mg/kg, or 30 mg/kg of the thermolysin digest of β-CG was orally administered as a test substance (n=11).

Figure 13:
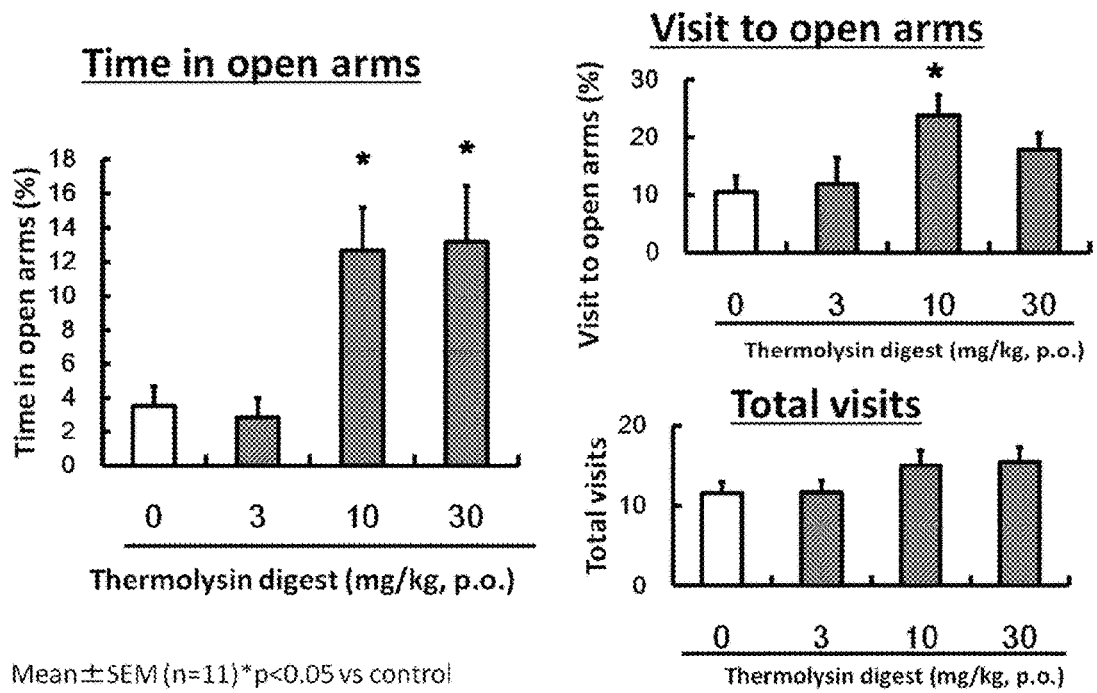
FIG. 13 shows the results of the elevated plus-maze test in mice to which an enzymatic digest was orally administered.

FIG. 13 shows the results. The percentage of time spent in the open arms was significantly increased when the digest was orally administered in an amount of 10 mg/kg or more. The percentage of the number of entries into the open arms was also significantly increased when the digest was orally administered in an amount of 10 mg/kg. On the other hand, no significant difference was observed in the total number of entries, which shows the amount of activities.

Example 10: Elevated Plus-Maze Test (Peptide)

The elevated plus-maze test was performed using mice to which 0.1 mg/kg, 0.3 mg/kg, or 1 mg/kg of the peptide LSSTQAQQSY (SEQ ID NO: 1) was administered as a test substance (n=18-19).

Figure 14:
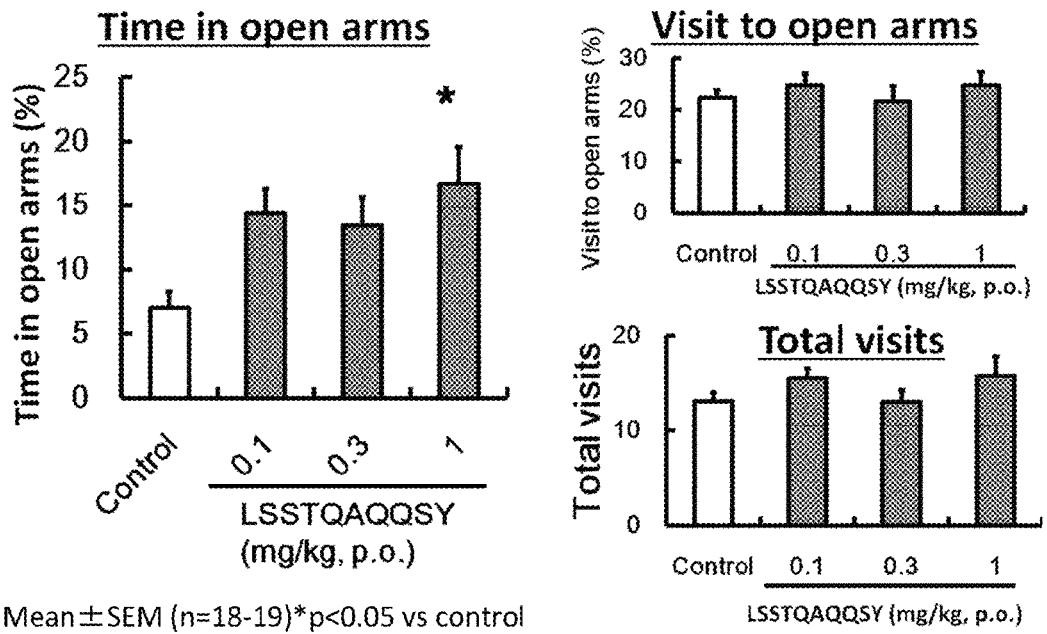
FIG. 14 shows the results of the elevated plus-maze test in mice to which a peptide (LSSTQAQQSY (SEQ ID NO: 1)) was orally administered.

FIG. 14 shows the results. The percentage of time spent in the open arms was significantly increased when the peptide was orally administered in an amount of 1 mg/kg. On the other hand, no significant difference was observed in the total number of entries, which shows the amount of activities.

Example 11: Open Field Test (Peptide)

The open field test was performed using mice to which 0.1 mg/kg, 0.3 mg/kg, or 1 mg/kg of the peptide LSSTQAQQSY (SEQ ID NO: 1) was administered as a test substance (n=4-5).

Figure 15:
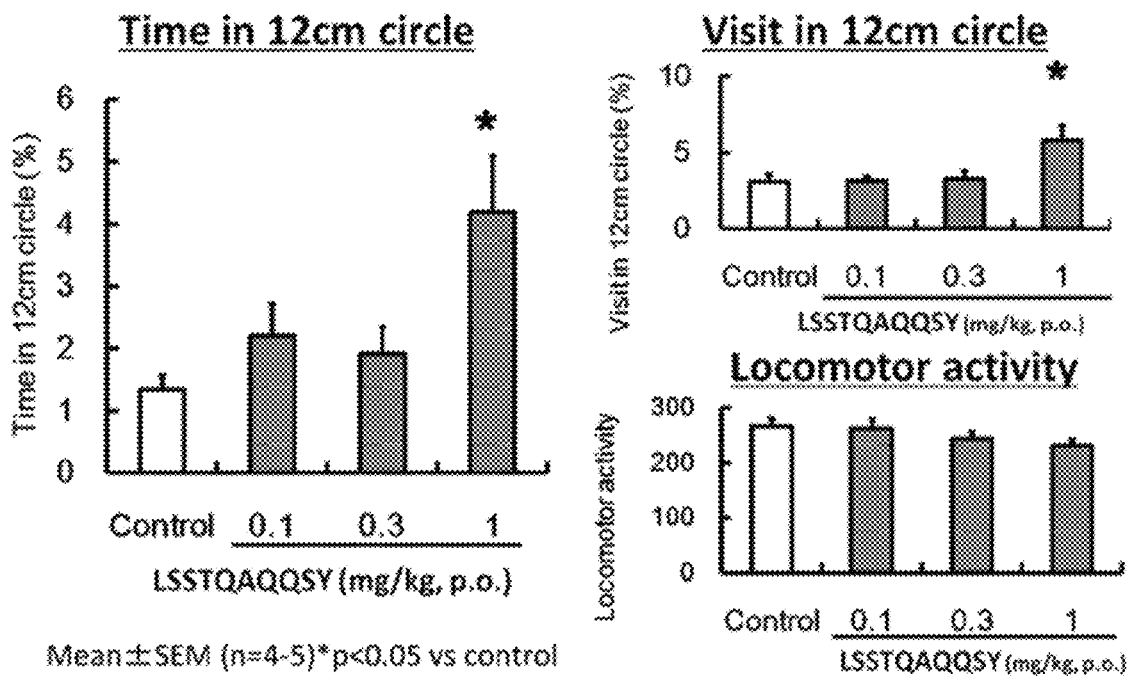
FIG. 15 shows the results of the open field test in mice to which a peptide (LSSTQAQQSY (SEQ ID NO: 1)) was orally administered.

FIG. 15 shows the results. The time spent in the center circle (open field) and the number of visits to the center circle (open field) were significantly increased when the peptide was orally administered in an amount of 1 mg/kg. On the other hand, no significant difference was observed in the amount of activities.

Example 12: Tail Suspension Test (Peptides)

The peptide LSSTQAQQSY (SEQ ID NO: 1), the peptide LSSTQAQQSY amidated at the C-terminus (LSSTQAQQSY-NH$_2$) (SEQ ID NO: 8), the peptide LSSTQAQQSW (SEQ ID NO: 6), and the peptide LSSTQAQQSF (SEQ ID NO: 7) were used as test substances. The tail suspension test was performed using mice to which 0.3 mg/kg of each test substance was individually orally administered (n=11-12).

Figure 16:
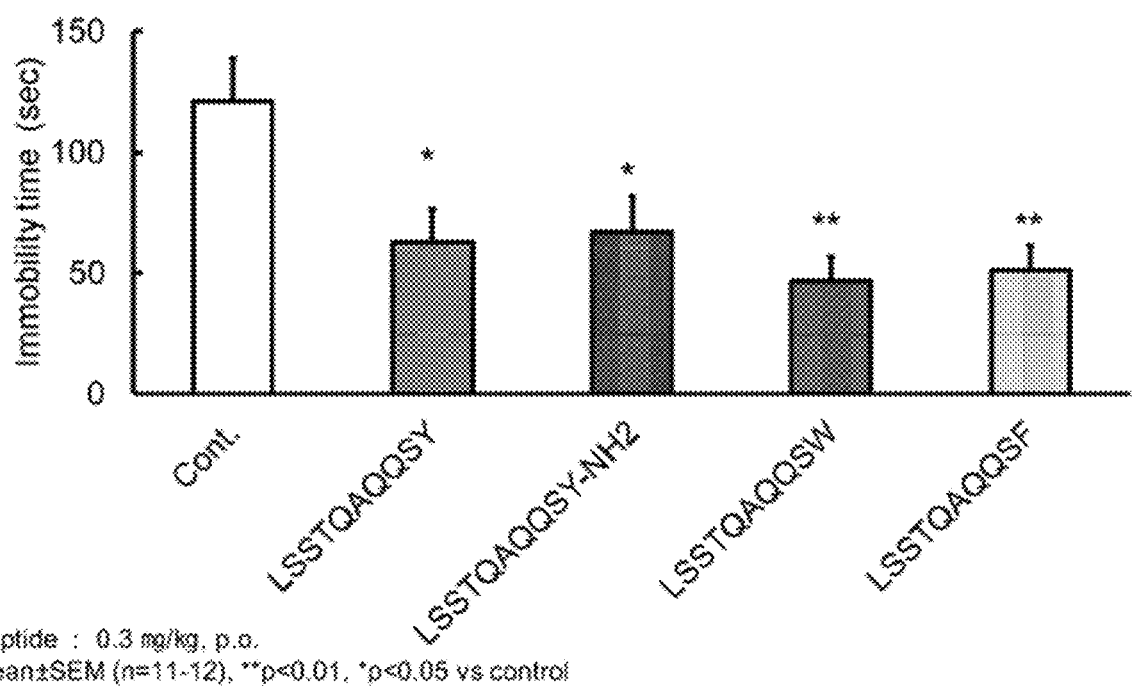
FIG. 16 shows the results of the tail suspension test in mice to which each peptide (LSSTQAQQSY (SEQ ID NO: 1); LSSTQAQQSY-$NH_2$ (SEQ ID NO: 8); LSSTQAQQSW (SEQ ID NO: 6); LSSTQAQQSF (SEQ ID NO: 7)) was individually orally administered.

FIG. 16 shows the results. No significant reduction in the immobility time was observed in any case compared with the case of using the peptide LSSTQAQQSY (SEQ ID NO: 1). This result revealed that not one of the N-terminal side and the C-terminal side of the peptide LSSTQAQQSY (SEQ ID NO: 1) alone is important, and that the full-length 10-residue peptide achieves the strongest immobility time reducing effect.

The invention claimed is:

1. A peptide or salt thereof, wherein the peptide has an amino acid sequence consisting of LSSTQAQQSY (SEQ ID NO: 1).

2. A pharmaceutical composition comprising a therapeutically effective amount of the peptide of claim 1 or salt thereof as an active ingredient.

3. The pharmaceutical composition of claim 2, wherein the amount of the peptide in the pharmaceutical composition is 0.01% by weight to 100% by weight of the pharmaceutical composition.

4. The pharmaceutical composition of claim 2, wherein the amount of the peptide in the pharmaceutical composition is 1% by weight to 90% by weight of the pharmaceutical composition.

5. A food product comprising a therapeutically effective amount of the peptide of claim 1 or salt thereof.

6. The food product of claim 5, wherein the amount of the peptide in the food product is 0.01% by weight to 100% by weight of the food product.

7. The food product of claim 5, wherein the peptide is an additive.

8. A method for treating a subject suffering from or at risk of suffering from diminished motivation, depression, or mood disorder, comprising administering a therapeutically effective amount of the peptide of claim 1 or salt thereof to the subject.

9. The method of claim 8, wherein the subject is suffering from or at risk of suffering from diminished motivation.

10. The method of claim 8, wherein the subject is suffering from or at risk of suffering from depression.

11. The method of claim 8, wherein the subject is suffering from or at risk of suffering from mood disorder.

12. A method for treating a subject suffering from or at risk of suffering from diminished motivation, depression, or mood disorder, comprising administering a therapeutically effective amount of the pharmaceutical composition of claim 2 to the subject.

13. The method of claim 12, wherein the subject is suffering from or at risk of suffering from diminished motivation.

14. The method of claim 12, wherein the subject is suffering from or at risk of suffering from depression.

15. The method of claim 12, wherein the subject is suffering from or at risk of suffering from mood disorder.

16. A method for treating a subject suffering from or at risk of suffering from diminished motivation, depression, or mood disorder, comprising administering a therapeutically effective amount of the food product of claim 5 to the subject.

17. The method of claim 16, wherein the subject is suffering from or at risk of suffering from diminished motivation.

18. The method of claim 16, wherein the subject is suffering from or at risk of suffering from depression.

19. The method of claim 16, wherein the subject is suffering from or at risk of suffering from mood disorder.

* * * * *